(12) United States Patent
Eubanks et al.

(10) Patent No.: US 9,108,027 B2
(45) Date of Patent: Aug. 18, 2015

(54) INTERVENTIONAL CATHETER HOUSING ASSEMBLIES INCORPORATING GUIDE WIRE BRAKES AND MANAGEMENT SYSTEMS

(71) Applicant: Boston Scientific Limited, Hamilton HM11 (BM)

(72) Inventors: Shannon Eubanks, Woodinville, WA (US); Michael David Nelson, Seattle, WA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

(21) Appl. No.: 13/777,972

(22) Filed: Feb. 26, 2013

(65) Prior Publication Data

US 2014/0243734 A1 Aug. 28, 2014

(51) Int. Cl.
*A61M 25/09* (2006.01)
(52) U.S. Cl.
CPC .............. *A61M 25/09041* (2013.01); *A61M 2025/09125* (2013.01)
(58) Field of Classification Search
CPC ............ A61M 25/09041; A61M 25/0113; A61M 25/0169; A61M 2025/0177; A61M 2025/09116
USPC .......... 604/528–532, 164.01, 164.04, 164.07, 604/164.11, 146.13; 600/585
See application file for complete search history.

(56) References Cited

U.S. PATENT DOCUMENTS

| 6,149,663 | A | 11/2000 | Strandberg et al. |
| 6,565,588 | B1 | 5/2003 | Clement et al. |
| 6,599,265 | B2 * | 7/2003 | Bon ........................... 604/95.01 |
| 6,818,001 | B2 | 11/2004 | Wulfman et al. |
| 7,344,546 | B2 | 3/2008 | Wulfman et al. |
| 7,390,323 | B2 | 6/2008 | Jang |
| 7,632,241 | B2 | 12/2009 | Raijman et al. |
| 7,674,272 | B2 | 3/2010 | Torrance et al. |
| 7,713,231 | B2 * | 5/2010 | Wulfman et al. .......... 604/93.01 |
| 7,713,235 | B2 * | 5/2010 | Torrance et al. .............. 604/118 |

(Continued)

FOREIGN PATENT DOCUMENTS

WO 20008042987 A2 4/2008

OTHER PUBLICATIONS

Bayer Medical Care Inc., "International Search Report and Written Opinion," Int'l Patent Application No. PCT/US2014/017842, filed Feb. 21, 2014 (May 16, 2014).

*Primary Examiner* — Nicholas Lucchesi
*Assistant Examiner* — Weng Lee
(74) *Attorney, Agent, or Firm* — Seager, Tufte & Wickhem, LLC

(57) ABSTRACT

Interventional catheter assemblies that operate over a guide wire are disclosed. Specifically, an elongated flexible catheter is associated at its proximal end with a housing having a guide wire port where the guide wire exits the housing. The housing additionally incorporates a guide wire brake mounted within a slot positioned a distance from the guide wire port for engaging and releasing a guide wire. The slot is generally arranged at an angle to the path of the guide wire as it exits the guide wire port. When the guide wire is clamped in the angled slot, variable lengths of exposed guide wire accumulate in a substantially unrestrained condition when the flexible catheter is advanced and retracted relative to the guide wire, allowing movement of the distal end of the catheter over considerable distances without repositioning and re-clamping the proximal end of the guide wire.

18 Claims, 8 Drawing Sheets

(56) References Cited

U.S. PATENT DOCUMENTS

| | | |
|---|---|---|
| 8,092,397 B2 * | 1/2012 | Wallace et al. ............... 600/587 |
| 8,323,240 B2 * | 12/2012 | Wulfman et al. .......... 604/95.01 |
| 8,435,228 B2 * | 5/2013 | Wulfman et al. ............. 604/528 |
| 2004/0235611 A1 * | 11/2004 | Nistal ........................... 475/331 |
| 2004/0243162 A1 * | 12/2004 | Wulfman et al. ............. 606/167 |
| 2006/0041245 A1 * | 2/2006 | Ferry et al. .................... 604/510 |
| 2007/0282167 A1 * | 12/2007 | Barenboym et al. .......... 600/131 |
| 2009/0287188 A1 * | 11/2009 | Golden et al. ................ 604/528 |
| 2011/0040238 A1 | 2/2011 | Wulfman |
| 2011/0105954 A1 * | 5/2011 | Cohen et al. .................. 600/585 |
| 2013/0035537 A1 * | 2/2013 | Wallace et al. .................... 600/8 |

* cited by examiner

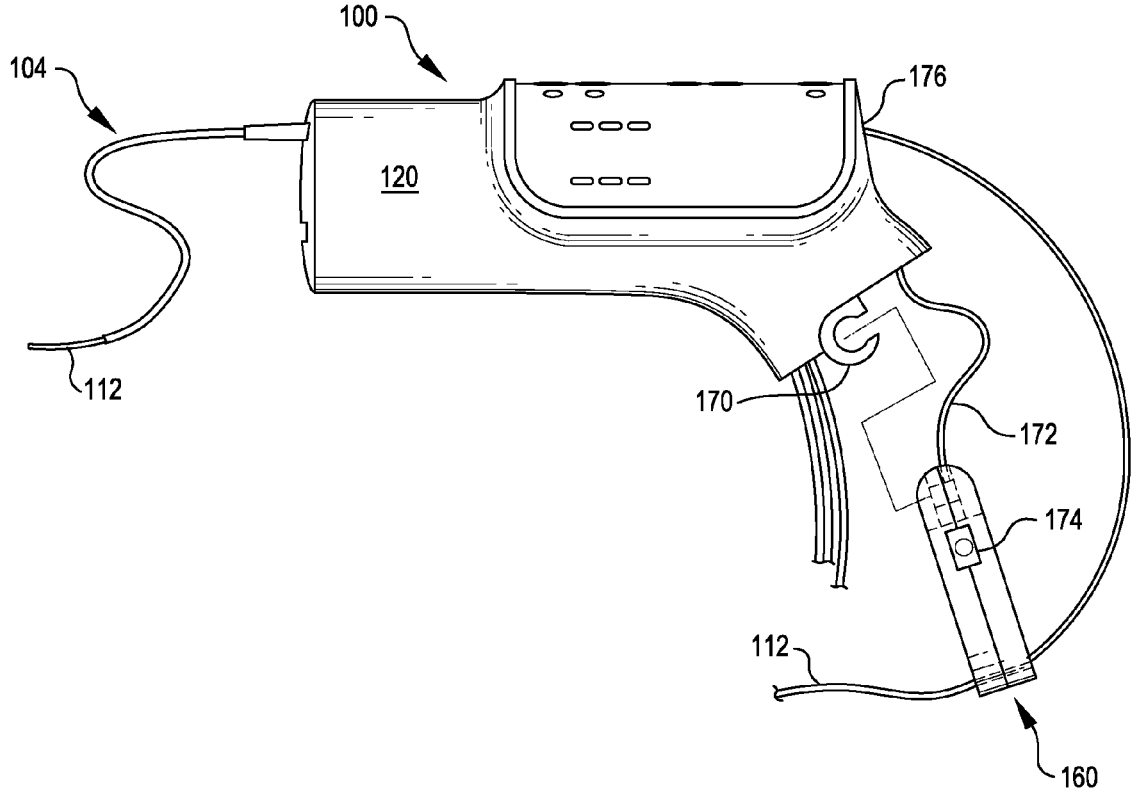

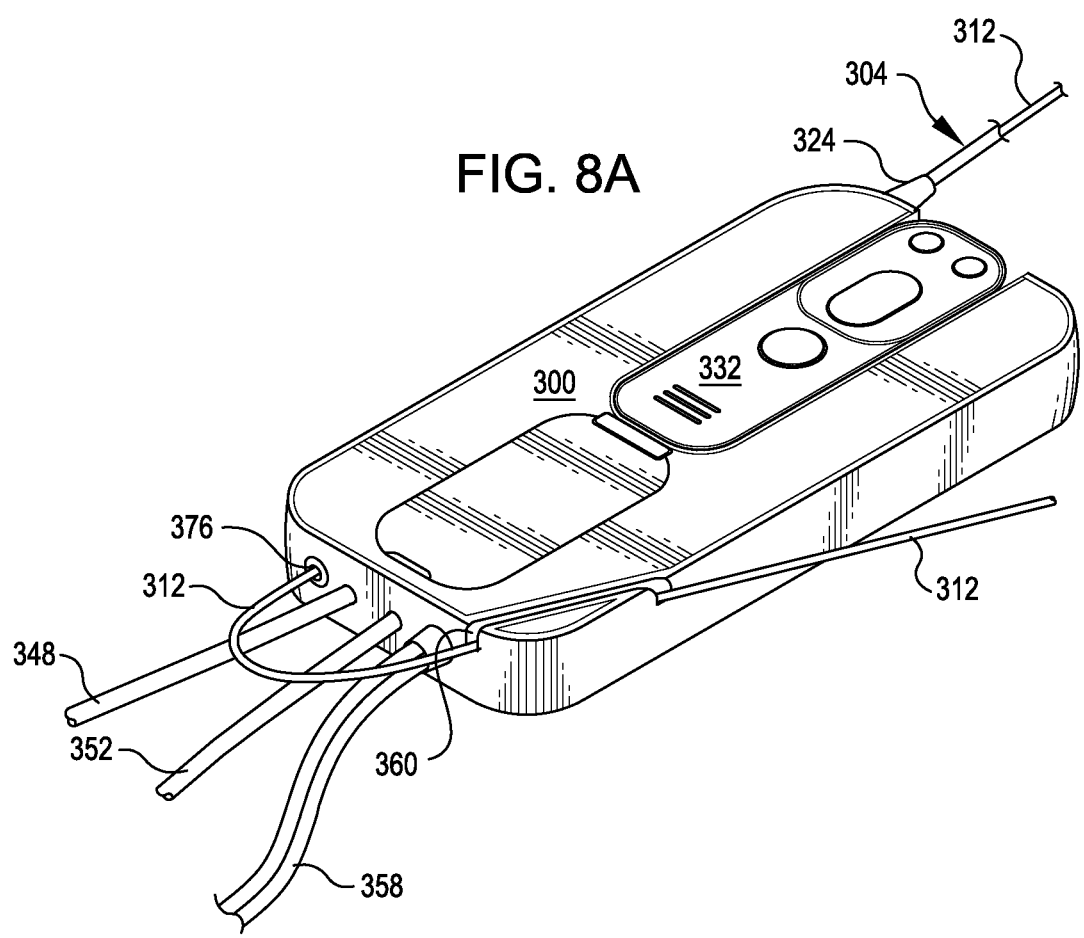

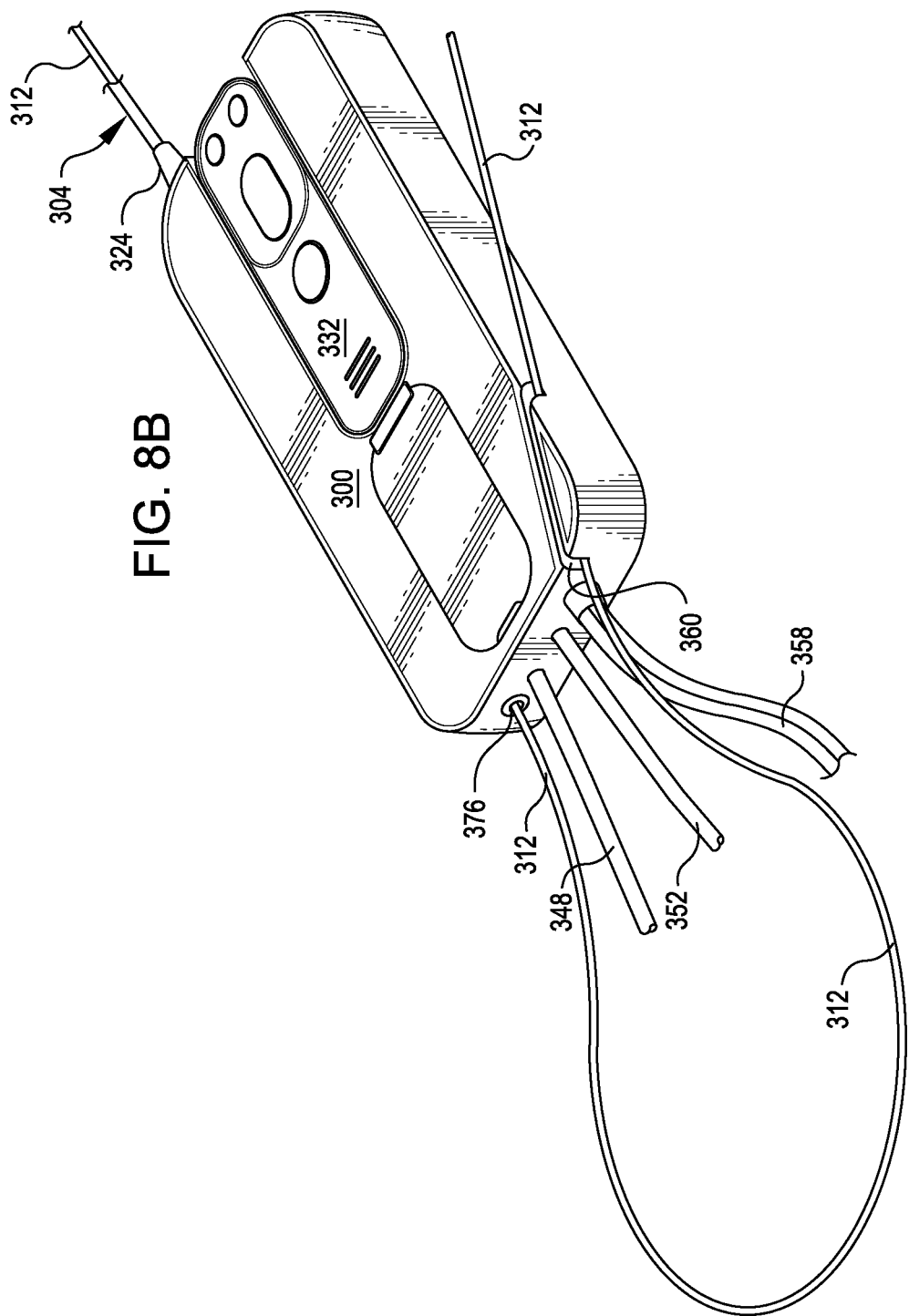

INTERVENTIONAL CATHETER HOUSING ASSEMBLIES INCORPORATING GUIDE WIRE BRAKES AND MANAGEMENT SYSTEMS

FIELD OF THE INVENTION

The present disclosure relates generally to interventional catheter assemblies that operate over a guide wire and relates, more particularly, to interventional catheter housing assemblies having a guide wire brake and a guide wire management system for use during procedures involving the placement and use of interventional catheters.

BACKGROUND OF THE INVENTION

Interventional techniques for removing disease such as atherosclerotic plaque, thrombus and other types of material forming obstructions and partial obstructions from internal body lumens or cavities using interventional catheters are well-established. Interventional catheters may employ operating heads that break down and/or remove occlusive material using mechanical structures such as cutter assemblies, abrasive materials and/or shaped tools, excision devices, ablation instruments employing modalities such as RF, laser or radiation-induced ablation modalities, ultrasound, fluid jets or fluid agitation and the like. Other types of interventional catheters may provide fluid infusion and/or aspiration alone, or in combination with another diagnostic or treatment modality. Many of these systems involve placement of a guiding catheter and/or guide wire prior to introduction of the interventional catheter, facilitating navigation of the interventional catheter to the target operating site and manipulation of the interventional catheter at the target site over the guide wire.

Many material removal devices and interventional catheters incorporate mechanical aspiration systems to remove the ablated material from the site and some systems incorporate or are used in conjunction with other mechanisms such as distal filters for preventing removed material from circulating in the blood stream. Some interventional catheter systems incorporate or are used in conjunction with a fluid infusion system providing delivery of fluids to an interventional site. Interventional catheter systems may also incorporate or be used in conjunction with imaging systems and other types of complementary and/or auxiliary tools and features that facilitate desirable placement and operation of the system during an interventional procedure.

Interventional catheters are generally mounted to controller housing drive mechanisms, fluid manifolds and management systems, and the like, at a proximal end of the catheter. Some types of interventional catheters employ a single operational and control component interfacing with and mounted to the interventional catheter. In devices that interface with a single operating and control component, system operating components may be housed in the control component and user interface controls for operating the catheter and operating head are provided on the operating and control component. Various control features for activating and operating the interventional catheter, its aspiration and/or infusion systems, and/or its operating head may be provided. Status indicators, system read-outs and operating information may also be provided on interventional catheter operating and control components.

Some interventional catheter systems may employ both a console-type controller that houses non-disposable components such as pumps, drive systems, electrical, electronic, vacuum and fluid control systems, and the like, as well as another intermediate control device that provides operator interfaces and control options and, in some cases, feedback information. The intermediate control device is typically located at or near a proximal end of the interventional catheter, and may be positioned within or close to the sterile field during a procedure. Interventional catheter systems employing both a console-type controller and an intermediate control device are described, for example, in PCT International Publication WO 2008/042987 A2, the disclosure of which is incorporated herein by reference in its entirety. Patients may also be monitored during an interventional procedure using separate or integrated systems, such as fluoroscopic or other visualization systems, vital sign monitoring systems, and the like.

Many interventional catheter systems are used in combination with a guide wire, which is navigated to a target intervention site and then aids safe navigation of the interventional catheter, over the guide wire, to the target site. The guide wire also facilitates positioning and movement of the interventional catheter over the guide wire at the target interventional site during the interventional procedure. When interventional catheter systems are employed as atherectomy or thrombectomy devices, for example, a guide wire is generally introduced into a patient's vasculature and advanced until its distal end is positioned at a location distal to the occlusion and the target intervention site. The interventional catheter is then advanced over the guide wire to a location just proximal to the occlusion. During an intervention, the distal end of the interventional catheter is generally advanced and retracted over the guide wire through the interventional site in distal and proximal directions, respectively, at least once and sometimes repeatedly, to remove occlusive tissue. Many other types of interventional catheter systems also involve translation of an interventional catheter over a guide wire prior to and/or during an intervention.

The guide wire generally traverses an internal guide wire lumen in the interventional catheter assembly and is generally routed into and through a controller or housing provided at the proximal end of the interventional catheter, exiting the controller at another location. A guide wire brake or clamp is generally provided within or in association with the controller, or in association with a proximal end of the interventional catheter, permitting the operator to clamp the guide wire in a fixed position. The guide wire is generally clamped following positioning of the guide wire and interventional catheter at the target interventional site, and during manipulation of the interventional catheter over the guide wire during an intervention.

When the guide wire is clamped following positioning of an interventional catheter in proximity to an interventional site and the interventional catheter is advanced distally over the clamped guide wire, the relative displacement of the catheter over the clamped guide wire in a distal direction exposes an equivalent length of guide wire between the proximal end of the catheter and the guide wire clamp. The excess guide wire exposed at the proximal end of the catheter as the interventional catheter is advanced distally generally accumulates within the controller or housing, or elsewhere between the proximal end of the interventional catheter and the guide wire brake. As the interventional catheter is retracted (i.e., moved proximally over the guide wire), the excess guide wire length accumulated at the proximal end of the interventional catheter is taken up and additional guide wire length is exposed, again, at the intervention site distal to the interventional catheter. This dynamic change in the relative positions of the guide wire and interventional catheter, resulting in variable lengths of exposed guide wire between the proximal end of the interventional catheter and the guide wire brake, is generally difficult to accommodate and presents guide wire management challenges.

Guide wires are relatively stiff along their longitudinal axes, and they tend to deform or kink or bend unacceptably when constrained in a space too small to accommodate the full length of the guide wire. Interventional catheter controllers mounted to the proximal end of an interventional catheter are generally relatively compact and thus provide limited space to accommodate the changes in guide wire length between the proximal end of the interventional catheter and the guide wire clamp as the interventional catheter is advanced distally over the guide wire. Because there is generally limited space for accommodating changes in guide wire length between the proximal end of the interventional catheter and the guide wire brake, operation of an interventional catheter over a guide wire for any substantial length generally requires repeated releasing and reclamping of the guide wire as the operating head is advanced and retracted during an intervention. This is particularly problematic when an interventional site, such as a lesion in a blood vessel, is relatively long. Readjustment and reclamping of the guide wire during the procedure as the operating head is repeatedly advanced and repeatedly retracted, complicates and prolongs the interventional procedure, which is undesirable and generally increases the risks of the intervention.

U.S. Pat. No. 7,713,231 discloses an extendible, telescoping guide wire support mounted in an intermediate controller device housing some of the interventional catheter operating systems. The telescoping guide wire support adjusts between a shorter, substantially folded condition and a longer, substantially extended condition to support the guide wire as the catheter and/or operating head are advanced and retracted over a clamped guide wire at the interventional site. This arrangement improves guide wire management during the operation of advanceable operating heads, but it still requires repeated releasing and reclamping of the guide wire when the interventional site, e.g., the length of a lesion, exceeds the length of the telescoping guide wire support device and the space allotted for the support device in the controller housing.

While considerable prior art exists relating to guide wire design, methods of using guide wires with interventional catheters, and guide wire brakes and clamps, there remains a need for improved performance of interventional catheter assemblies over guide wires and improved integration of guide wire brakes with interventional catheter assemblies, as well as for improved devices and methods for manipulating, adjusting, limiting or otherwise managing the relative movement and/or positioning of guide wires relative to interventional catheters and/or controllers during an intervention. Improved guide wire integration and improved management of guide wire positioning; relative to an interventional catheter assembly and/or controller result in faster, safer and more effective catheter-based interventional treatments.

SUMMARY

Interventional catheters and associated housing assemblies disclosed herein may be employed to rapidly and effectively aspirate, irrigate, deliver devices or materials to and/or remove unwanted material from internal body sites, such as internal cavities, lumens or passageways. Interventional catheter assemblies and guide wire brake and management systems may be adapted to many different types of interventional catheter assemblies that are useful in a wide variety of interventions within a variety of internal body sites, such as body cavities, body lumens or passageways such as blood vessels, lumens in the urinary system and in male and female reproductive organs, pulmonary lumens and gas exchange cavities, nasal and sinus passageways, and the like. Interventional catheter assemblies as disclosed herein may be used, for example, for aspirating and/or irrigating target interventional sites, as well as for removing undesired material from native blood vessels such as native coronary, renal, cranial, peripheral and other blood vessels, as well as from artificial or grafted vessels such as saphenous vein grafts, and the like. Undesired material that is aspirated or removed using interventional catheter assemblies and control systems disclosed herein may be disease material such as atherosclerotic plaque, calcified plaque, thrombus, or other types of deposits, gallstones, a valve or portion thereof, undesired fluids, and the like. In certain embodiments, the interventional catheter assemblies disclosed herein are employed in the treatment of cardiovascular or peripheral artery disease (PAD) to remove disease material from blood vessels, including peripheral blood vessels.

Interventional catheter assemblies comprise an elongated, flexible catheter that is at least partially inserted into and navigated through a lumen and/or cavity within a patient's body while an operator controls the system externally of the patient's body. The elongated catheter incorporates a guide wire lumen or another mechanism for routing the catheter over, or along, a guide wire. Some of the interventional catheter assemblies disclosed herein incorporate a component referred to as an "operating head," which is generally positioned at or near the distal end of the interventional catheter. Various types of operating heads may be used in connection with interventional catheter assemblies disclosed herein, including operating heads that break down and/or remove occlusive material using mechanical structures such as cutter assemblies, abrasive materials and/or shaped tools, excision devices, ablation instruments employing modalities such as RF, laser or radiation-induced ablation modalities, ultrasound, fluid jets or fluid agitation and the like. As used herein, "proximal" refers to a direction toward the system controls and the operator along the path of the catheter system, and "distal" refers to the direction away from the system controls and the operator along the path of the catheter system toward or beyond a terminal end of the operating head.

Fluidic communication between the distal end of the elongated catheter and, in some embodiments, the operating head) and externally positioned components of the interventional catheter system may be provided through one or more sealed passageways of the catheter system. Sealed aspiration and/or infusion lumens provided in a catheter generally interface with aspiration and/or infusion conduits at a manifold located within or associated with a housing, and the aspiration and/or infusion conduits in turn interface with aspiration and/or infusion systems, such as pumps, vacuum devices, infusate sources, and the like, provided in connection with interventional catheter operating and control systems. Communication systems or pathways may also be provided for delivery of power, for rotationally driving (or otherwise operating) and translating an operating head, for implementing various control features, and the like. The system components described below are described as exemplary components and are not intended to limit the scope of the present disclosure or claims.

In some embodiments an interventional catheter operating head, or a component of an operating head, may be operably connected to a rotatable and/or axially translatable drive shaft, drive system and one or more control systems. A rotatable operating head may, for example, incorporate one or more cutter or ablation elements. In some embodiments, the operating head may comprise an abrasive surface or an abrasive material provided on a surface of a rotational element. In alternative embodiments, an operating head may comprise another type of material removal device, such as a plaque excision device, a laser ablation or high frequency ultrasound ablation device, or a radio frequency or heat-producing or electrical device that operates to remove unwanted material from body lumens or cavities and generally does not rotate during operation. These types of ablation devices are well known in the art.

The interventional catheter assembly and/or operating head may be operated and advanced by operator manipulation and mechanical systems, or by a variety of other systems, including electrical systems, radio frequency, sterotactic and other remotely control systems, magnetic systems and other systems or modalities suitable for remote operation of an operating head. The interventional catheter assembly may incorporate aspiration and/or infusion features, device or tool delivery features, and/or material removal features, and it may provide additional functionalities such as ultrasound guidance (or guidance using another modality), various types of visualization and imaging features, and the like.

Interventional catheter systems described herein are used in conjunction with a flexible guide wire that is navigated through internal passageways or cavities, such as blood vessels, to a target intervention site. Simple aspirating and/or infusing interventional catheters, for example, may be navigated to, and then through, an interventional site over a clamped guide wire while operating the aspiration and/or infusion systems to aspirate material from the site, and/or to deliver desired fluids to the site. Atherectomy and thrombectomy catheters are generally navigated to an interventional site over a guide wire and then advanced into and through an obstruction at the target site, while operating, to remove material. The extent of relative movement of the distal end of the interventional catheter over the guide wire may depend on the dimension, generally the length, of the interventional site, the condition of the interventional site, such as the nature and extent of an occlusion, the condition and configuration of the vessel, and the like.

The present disclosure provides interventional catheter assemblies that are navigated to and positioned at an intervention site by translation over a guide wire and incorporate a guide wire management system associated with a housing assembly permitting the interventional catheter, and/or an operating head, to be advanced and retracted for variable distances over a guide wire without releasing and reclamping the guide wire. From an operational standpoint, the interventional catheter is typically loaded over or along a guide wire, and the distal portion of the guide wire is then inserted into and navigated through the patient's vasculature to the target intervention site Following placement of the guide wire, the interventional catheter may be advanced through the vasculature, over the guide wire, and positioned in proximity to a target intervention site. Frictional forces generally hold the guide wire and interventional catheter in position relative to one another, and relative to a target intervention site, until the interventional catheter and/or operating head is activated.

The guide wire is typically clamped at a location proximal to a proximal end of the interventional catheter prior to advancing the interventional catheter. Activation of high speed rotational catheters and/or operating heads breaks the static friction between the guide wire and the rotational drive system, allowing the rotational catheter, drive system and operating head to move readily over the static (clamped) guide wire as the operating head is advanced and/or retracted through the target site. Guide wire management systems and methods of the present disclosure provide a guide wire buffer zone positioned between the location where the guide wire exits the interventional catheter (or the controller) and the guide wire clamp that allows variable lengths of exposed guide wire to accumulate in a generally unsupported and unconstrained condition as the interventional catheter is advanced distally over the guide wire during an intervention.

Because guide wires used with interventional catheters have a substantial degree of stiffness along their longitudinal axis to provide the required "pushability," the unrestrained guide wire that accumulates within the guide wire buffer zone forms a curved profile. The length of guide wire exposed in the guide wire buffer zone following placement of the guide wire and interventional catheter at the intervention site and clamping of the guide wire, and prior to advancing the interventional catheter into an intervention site, is generally relatively short, and the exposed, generally unsupported guide wire forms a gently curved configuration. As the interventional catheter is advanced distally over the guide wire into and through the intervention site, the length of guide wire exposed in the guide wire buffer zone increases, forming curves having progressively larger profiles. The configuration of the guide wire buffer zone may be such that long lengths of guide wire may accumulate, substantially unsupported, in the guide wire buffer zone, forming larger and larger profile curves. The curved profile of the guide wire accumulated in the buffer zone may take the form of many curved shapes that change profile, as necessary, as the length of guide wire present in the guide wire buffer zone changes.

When the interventional catheter is retracted proximally over the guide wire following an advance, the process is reversed. The relative axial movement of the interventional catheter with respect to the guide wire during retraction exposes more guide wire distally in proximity to the intervention site and diminishes the excess length of guide wire accumulated in the guide wire buffer zone. As the length of guide wire exposed in the buffer zone diminishes, curves having progressively smaller profiles are formed. In this way, the interventional catheter and operating head may be advanced and retracted for long distances over the guide wire without requiring guide wire clamp adjustments and without compromising or damaging the guide wire.

Guide wire management systems of the present disclosure thus provide that the clamping portion of the guide wire brake is positioned (or positionable) at a distance from the location where the guide wire exits the controller (or the interventional catheter or a housing), forming a guide wire buffer zone in which the guide wire is substantially unrestrained and generally unsupported. Variable lengths of guide wire may be conveniently accommodated in the guide wire buffer zone without changing the position of the controller, the interventional catheter, or the guide wire clamp, allowing the distal end of the catheter, and an (optional) operating head, to be advanced and retracted over the guide wire without repositioning the guide wire or adjusting the guide wire clamp. Associating and/or functionally integrating a guide wire brake and guide wire buffer zone with an interventional catheter assembly in the arrangements disclosed herein provides many advantages in terms of operator convenience, improved accuracy and precision in guide wire positioning and/or fixation, and better control of desired catheter and operating head motions and operation during an intervention. These advantages facilitate quicker interventions and require fewer operator manipulations, thereby improving the safety and efficacy of interventional procedures in general.

In general, an integrated guide wire buffer zone of the present disclosure is designed and configured to accommodate changes in the relative position of the distal end of the catheter (and/or operating head) with respect to a fixed guide wire, with the guide wire buffer zone operating to provide a space for effectively allowing excess guide wire length to accumulate as the operating head is advanced, and allowing the excess guide wire length to be taken up as the operating head is retracted. The guide wire buffer zone of the present disclosure is designed, incorporated and functionally integrated with the catheter assembly, the controller or housing, and the guide wire brake, providing a guide wire management system that effectively and conveniently accommodates changes in exposed guide wire length at the proximal end of the catheter and controller as the catheter and operating head are advanced and retracted during an interventional procedure.

In some embodiments, a guide wire management system according to the present disclosure comprises a controller and/or a housing and a guide wire brake mechanism associated with it. During an intervention, the guide wire generally transits a guide wire lumen in the interventional catheter assembly and transits a generally unobstructed guide wire path in the controller and/or housing positioned at a proximal end of the interventional catheter assembly. The guide wire exits the controller housing at a guide wire exit port. A guide wire brake (e.g., clamp) is positioned a distance from the guide wire exit port and may be positioned externally of and at a location proximal to the interventional catheter assembly and controller, or a guide wire brake may be positioned within or in association with the controller and/or the housing.

In some embodiments, the position of the guide wire clamp is adjustable, for example, allowing an operator to adjust the position of the guide wire clamp closer to or farther from the guide wire exit port. The space between the guide wire exit port and an externally located guide wire clamp location generally defines the integrated guide wire buffer zone positioned between the controller (and/or a proximal end of the interventional catheter assembly) and the guide wire clamp. When the guide wire clamp is positioned relatively closer to the guide wire exit port, a relatively small guide wire buffer zone is provided, allowing axial translation of the interventional catheter and operating head (e.g. advancement and retraction) over a relatively short distance without requiring repositioning of the guide wire and reclamping of the guide wire brake. When the guide wire clamp is positioned relatively further away from the guide wire exit port, a relatively large guide wire buffer zone is provided, allowing axial translation of the interventional catheter and operating head (e.g. advancement and retraction) over a relatively long distance without requiring repositioning and reclamping of the guide wire brake. The operator may position an adjustable guide wire clamp prior to and/or during an interventional procedure to provide a relatively small or large guide wire buffer zone, depending on the size and characteristics of the interventional site, the catheter and the guide wire, the type of intervention, the anticipated travel of interventional catheter and operating head advancements and retractions, and the like.

In one embodiment providing an adjustable guide wire clamp, the guide wire clamp may be located, for example, at one end of a guide wire clamp housing, while an opposite end of the guide wire clamp housing is pivotably mounted to a controller housing. Providing a pivoting mounting for the guide wire clamp housing permits the guide wire clamp to be spaced a variable and selectable distance from the guide wire exit port, thus changing the dimensions of the guide wire buffer zone. This feature allows the configuration of the guide wire buffer zone to be adjusted and/or optimized by an operator prior to and/or during an intervention based on the antici-pated range of relative axial motion of the catheter and operating head and the length of guide wire exposed proximally during operation of the interventional catheter. In this embodiment, the position of the guide wire brake and the dimensions of the guide wire buffer zone may also be changed during an intervention to accommodate unanticipated conditions without slowing the procedure, reclamping the guide wire, or repositioning any other components of the interventional catheter assembly.

In some interventional catheter systems of the present disclosure, the guide wire clamp housing and guide wire clamp may be detachable from the controller. This allows the guide wire clamp to be mounted and/or positioned independently of an intermediate controller or housing during use, if desired. This feature may be particularly useful in cases where the intervention requires operation of the operating head (and/or catheter assembly) over relatively large distances, requiring the guide wire buffer zone to be correspondingly large. The guide wire clamp housing may incorporate a mounting mechanism for detachably mounting the housing, and the guide wire clamp, to a variety of stationary structures during use. Suitable detachable mounting mechanisms are well known in the art.

In some embodiments, as noted above, a guide wire buffer zone is positioned externally of a proximal interventional catheter controller or housing and provided as a space between the location where the guide wire exits the controller (e.g., guide wire exit port) and the location of the guide wire clamp. In interventional catheter systems that don't employ an intermediate controller or housing, the guide wire clamp may be positioned a predetermined or adjustable distance away from the location where the guide wire exits the proximal end of the interventional catheter. In these embodiments, the guide wire buffer zone accommodates variable lengths of guide wire in an unrestrained condition when the guide wire is clamped, as the distal end of the interventional catheter and/or operating head are advanced and retracted.

In some embodiments, the guide wire brake assembly may be provided within an interventional catheter housing assembly. In one exemplary embodiment, an interventional catheter assembly of the present disclosure comprises an elongated flexible catheter incorporating a guide wire lumen or track, as previously described, the catheter being associated at a proximal region with a housing containing various operational components. An operating head may be provided at or near a distal end of the elongated flexible catheter, and other systems and features may be incorporated in the interventional catheter assembly and/or the housing including, for example, aspiration and/or infusion features, and the like. A guide wire exit port is provided penetrating the housing for slidably receiving the guide wire and allowing the guide wire to exit the housing, extending generally proximally of the housing. A guide wire brake may be provided within the interventional catheter housing and accessed from the exterior of the housing, for example, through a slot provided in the housing and positioned a distance from the guide wire exit port. In some embodiments, the guide wire brake slot is angled with respect to the orientation of a guide wire as it exits the guide wire exit port. During operation, the guide wire is received through the catheter, exits the housing at the guide wire port, and is received within the slot, where the guide wire brake may be employed to clamp the guide wire. The area between the guide wire port and the slot entry forms a guide wire buffer zone, allowing variable lengths of exposed guide wire to accumulate in a substantially unrestrained, curved condition when the catheter is advanced and retracted relative to the guide wire. This allows movement of the distal end of the catheter over considerable distances without requiring repositioning and re-clamping of the proximal end of the guide wire.

It will be recognized that guide wire management systems of the present disclosure may be used with a variety of interventional catheter systems that are operated over a guide wire, regardless of the type of operating head employed. In various embodiments, the interventional catheter operating head may provide any type of treatment modality, e.g. cutting, diagnostics, imaging, energy deposition, device delivery, and the like.

BRIEF DESCRIPTION OF THE DRAWINGS

Illustrative embodiments of various aspects and elements of the present disclosure are described in greater detail in the following detailed description with reference to the accompanying illustrations and images, which are not intended to limit the scope of the claimed invention.

FIG. 7 is a schematic view of another embodiment of an interventional catheter assembly having a guide wire management system of the present disclosure with a detachable guide wire brake housing.

FIG. 8A is a schematic view showing an exemplary interventional catheter housing assembly having a guide wire management system employing a guide wire brake mounted to operate in a slot in the interventional catheter housing, illustrating an exemplary guide wire position and condition when the interventional catheter is positioned on a guide wire proximal to and near a target intervention site, as illustrated schematically in FIG. 4B.

FIG. 8B is a schematic view of an interventional catheter housing assembly and guide wire management system similar to that shown in FIG. 8A, illustrating an exemplary guide wire position and condition when the interventional catheter has been advanced on the guide wire through a target intervention site, as illustrated schematically in FIG. 6B.

DETAILED DESCRIPTION

Figure 1:
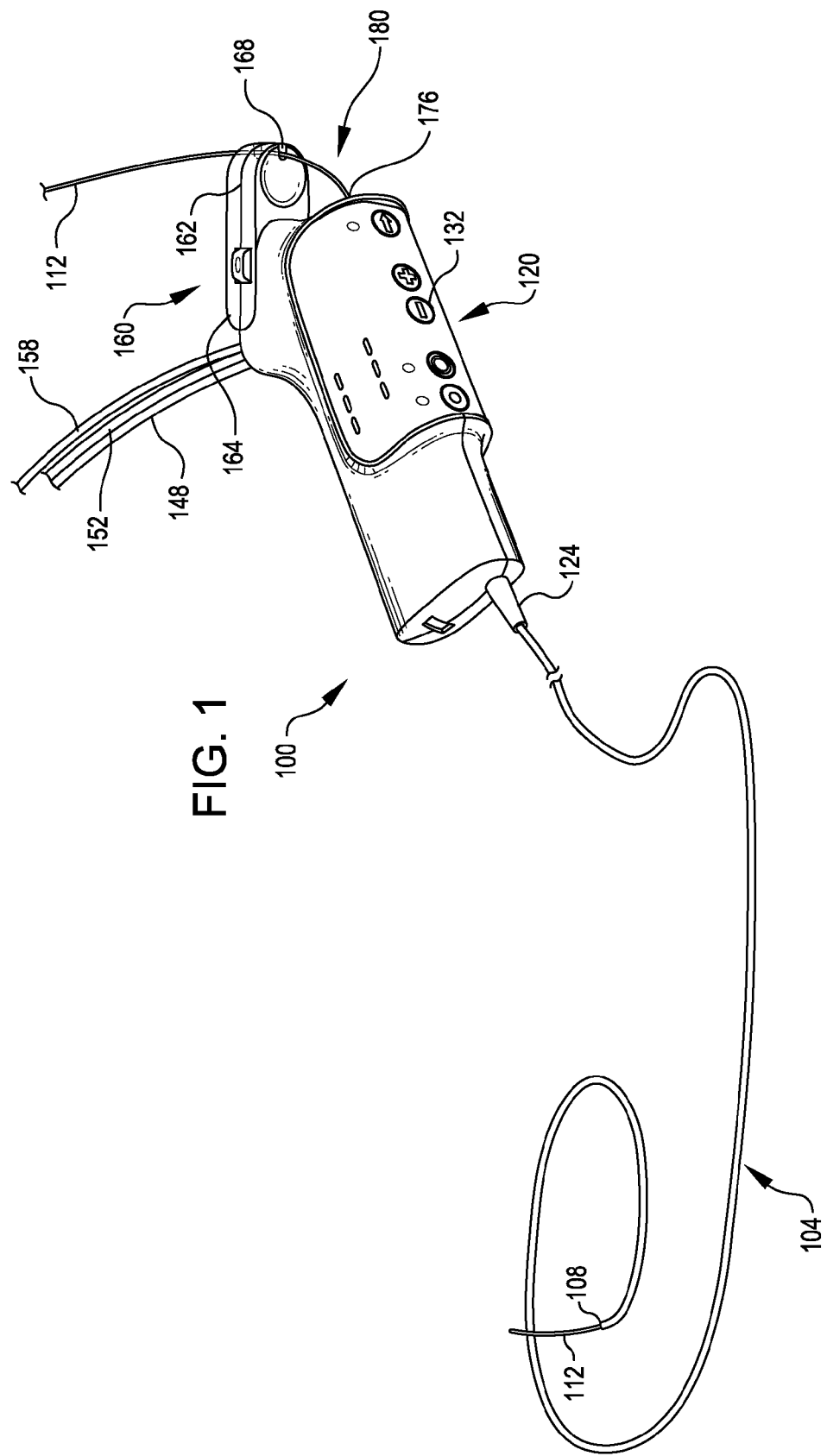
FIG. 1 is a schematic view of a one embodiment of an interventional catheter assembly of the present disclosure employing a guide wire management system.

FIG. 1 shows a schematic view of an illustrative interventional catheter system 100 comprising an elongated, flexible interventional catheter 104 having an operating head 108 positioned in proximity to its distal end, the operating head being configured to generate, transmit, deliver or otherwise provide a desired treatment modality to an interventional site within the patient. In one embodiment, operating head 108 comprises a rotatable, advanceable assembly that, with interventional catheter 104, is navigated to a desired interventional site over a guide wire and is then axially translated, i.e. advanced and retracted, over the guide wire during an intervention. Interventional catheter 104 may have appropriate sealed lumens for aspiration and/or infusion of liquids and may be in fluidic communication with aspiration and infusion systems positioned in a proximal controller or housing, or in a separate module.

Interventional catheter 104 is operably connected (or connectable) at its proximal end to a controller housing 120 at distal feedthrough 124. Controller housing 120 contains mechanisms and components such as drive motors, energy sources, electro-mechanical components, conduits, circuit boards, data processors, communication ports, fluid manifolds and the like, for operating the interventional catheter and/or the operating head. One or more user interface control features 132 (e.g., user operable switches and/or visual status indicators) may provide a user interface for one or more monitoring or control features of the interventional catheter assembly. In the embodiment illustrated in FIG. 1, aspiration conduit 148, infusion conduit 152 and electrical cable 158 enter controller housing 120 at a location spaced apart from the location of distal feedthrough 124, generally at its proximal end. Aspiration conduit 148 and infusion conduit 152 convey aspiration and infusion fluids between the interventional catheter and/or operating head 108 and aspiration and infusion components located elsewhere, such as in a reusable control console. Electrical cable 158 provides power, electronic communications, and the like to controller housing 120, interventional catheter 104 and/or operating head 108, as necessary to operate and control the interventional catheter system.

FIG. 1 schematically illustrates interventional catheter system 100 mounted "over" a guide wire 112 for illustrative purposes as it would be for operation of the interventional catheter and/or operating head during an intervention. Guide wire 112 transits an interventional catheter guide wire lumen in interventional catheter 104, and a distal end of guide wire 112 projects from a distal end of interventional catheter 104 and operating head 108. Guide wire 112 also traverses feedthrough 124 and controller housing 120, exiting controller housing 120 at a generally proximal location at guide wire exit port 176. Guide wire brake housing 160 is integrated with or associated with and/or mounted or mountable to controller housing 120 at an end region 164.

Guide wire brake housing 160 incorporates guide wire brake mechanism 168 through which guide wire 112 passes. Brake mechanism 168 is a user operable component that, in an open, release condition, allows the guide wire to rotate and translate freely and, in a closed, actuated condition, serves to clamp the guide wire and prevent the guide wire from moving either axially or rotationally with respect to the guide wire brake mechanism 168. This fixes the axial and rotational position of guide wire 112 with respect to the brake mechanism, the interventional catheter and operating head, and the intervention site, provided that the position of controller housing 120 (to which guide wire brake housing 160 is mounted) remains unchanged.

In the exemplary embodiment illustrated in FIG. 1, guide wire brake mechanism 168 is located at a first end region 162 of guide wire brake housing 160 generally opposite a second end region 164 of guide wire brake housing 160 mounted to controller housing 120. In the embodiment illustrated, guide wire brake mechanism 168 is also positioned a distance from and generally proximal to guide wire entry/exit port 176. The space between guide wire entry/exit port 176 and brake mechanism 168 defines a guide wire buffer zone 180 in which guide wire 112 is substantially unrestrained and generally unsupported. In the configuration shown in FIG. 1, guide wire buffer zone 180 is relatively small, and a relatively short length of guide wire 112 is present in the guide wire buffer zone. This represents a "neutral" condition of the guide wire in the guide wire buffer zone that corresponds to the relative positions of the guide wire and interventional catheter prior to advancing the interventional catheter distally over the guide wire at the intervention site.

Figure 2:
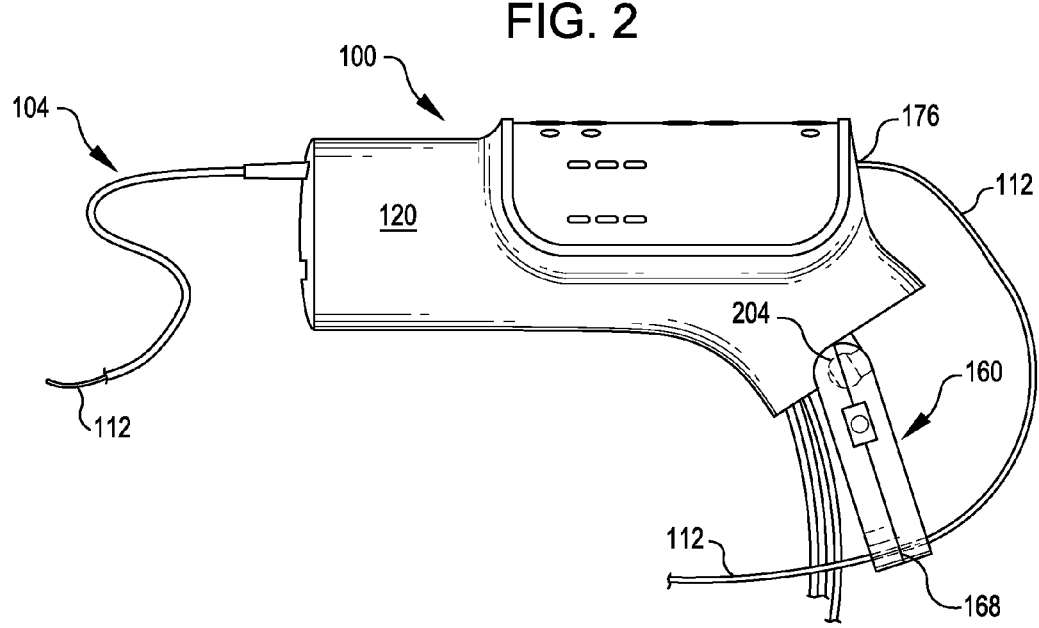
FIG. 2 shows a schematic view of another embodiment of an interventional catheter assembly having a guide wire management system illustrating a guide wire clamp position and guide wire buffer zone.

FIG. 2 shows another view of an interventional catheter assembly incorporating a guide wire management system according to one embodiment of the present disclosure, in this embodiment, the guide wire brake and housing may be similar to the guide wire brake and housing described above with reference to FIG. 1, but the placement of the guide wire clamp and housing with respect to the guide wire exit/entry port is different. In this embodiment, guide wire brake housing 160 is mounted on controller housing 120 to position the guide wire brake mechanism 168 at a relatively large distance from the guide wire entry/exit port 176. This arrangement of the brake mechanism 168 at a distance from the guide wire entry/exit port 176 provides a guide wire buffer zone between guide wire exit port 176 and brake mechanism 168 that is relatively large, thereby accommodating a longer length of guide wire in the buffer zone. This schematic drawing also represents a "neutral" condition of the guide wire passing through a larger guide wire buffer zone located between guide wire exit port 176 and brake mechanism 168 that corresponds to the relative positions of the guide wire and interventional catheter prior to advancing the interventional catheter distally over the guide wire at the intervention site. The relatively large guide wire buffer zone configuration illustrated in FIG. 2 allows the interventional catheter and operating head to travel a relatively long distance relative to the distal end of the guide wire and allows a relatively long length of guide wire to accumulate in the buffer zone without repositioning and/or reclamping the guide wire.

Guide wire management systems of the present disclosure are generally arranged such that the buffer zone formed between the guide wire entry/exit port and the guide wire clamp during an interventional procedure is sufficient to allow an unsupported and unconstrained guide wire transiting the guide wire buffer zone to form a curved profile in a neutral condition, and to allow the guide wire exposed in the buffer zone to form a larger curved profile as the interventional catheter is advanced and the guide wire accumulates in the guide wire buffer zone. Depending on the position and orientation of the guide wire brake housing with respect to the guide wire entry/exit port, the guide wire that accumulates in the guide wire buffer zone as the interventional catheter is advanced on the guide wire may form an arc, with the radius of curvature of the arc increasing as the length of guide wire accumulating in the buffer zone increases.

The distance between the guide wire entry/exit port and the guide wire clamp along a curved, neutral condition guide wire path is generally from about 2 cm to about 15 cm. In some embodiments, the distance between the guide wire entry/exit port and the guide wire clamp along a curved, neutral condition guide wire path may be from about 5 cm to about 12 cm. In some preferred embodiments, the distance between the guide wire entry/exit port and the guide wire clamp along a curved, neutral condition guide wire path is at least about 5 cm. The length of guide wire that may accumulate in the guide wire buffer zone, forming a curved profile without damaging the guide wire by kinking or bending, is generally from about 5 cm to about 60 cm.

It will be appreciated that many different configurations of guide wire clamps and housings may be employed in guide wire management systems of the present disclosure, and that the guide wire clamp and/or housing may be mounted and positioned in a variety of ways with respect to the guide wire entry/exit port to produce guide wire buffer zones having a variety of dimensions and locations.

Figure 3:
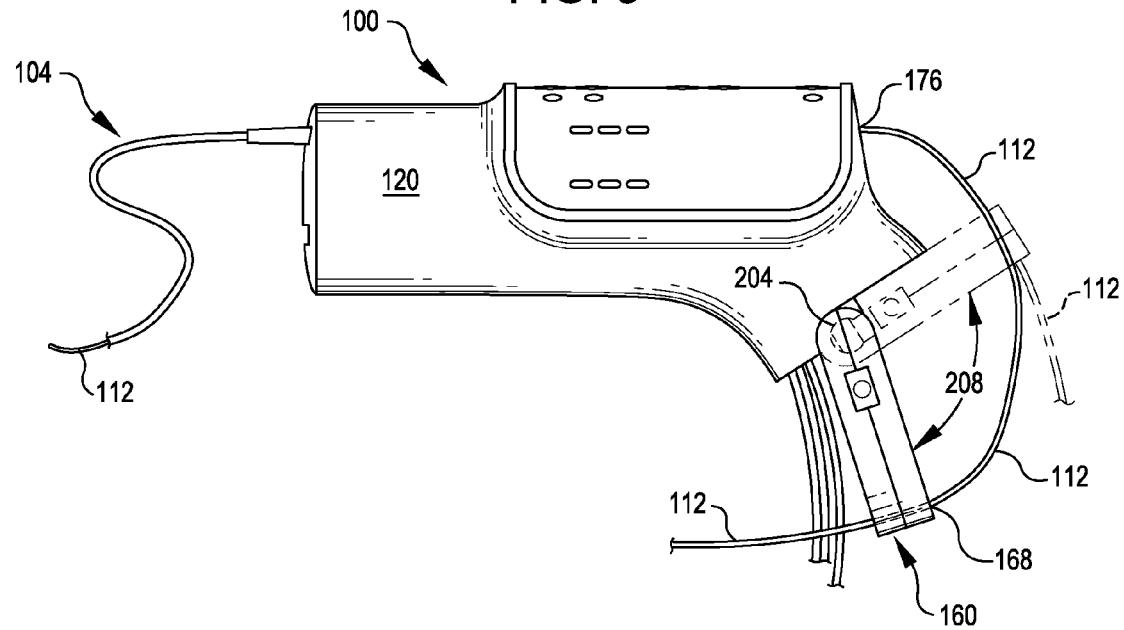
FIG. 3 shows a schematic view of an interventional catheter assembly having a guide wire management system employing a guide wire clamp that is adjustable to vary the size and configuration of the guide wire buffer zone.

FIG. 3 illustrates another interventional catheter assembly incorporating a guide wire management system according to another embodiment of the present disclosure. In this embodiment, guide wire brake housing 160 is connected and functionally integrated with controller housing 120 at pivot 204. Pivot mechanism 204 allows the guide wire brake housing 160 to rotate about the pivot between the position shown in dashed lines in FIG. 3, corresponding to the guide wire brake position illustrated in FIG. 1 and the position shown in solid lines, corresponding to the guide wire brake position illustrated in FIG. 2. In the embodiment of FIG. 3, guide wire brake housing is pivotable about pivot 204 through pivot angle 208. This allows an operator to select and modify the dimension and configuration of the guide wire buffer zone before, and/or during, an intervention.

The position of the guide wire brake housing 160 shown in dashed lines, which is substantially the position of the guide wire brake housing and clamp illustrated in FIG. 1, may represent one end of travel of a pivotably adjustable guide wire brake housing. In this condition, the pivot angle 208 is substantially zero and the guide wire buffer zone provided between guide wire entry/exit port 176 and brake mechanism 168 is relatively small. The position of guide wire brake housing 160, shown in solid lines in FIG. 3, which is substantially the position of the guide wire brake housing and clamp illustrated in FIG. 2, may represent the other end of travel of a pivotably adjustable guide wire brake housing, in this condition, pivot angle 208 is at least about 90°, and the guide wire buffer zone provided between guide wire entry/exit port 176 and brake mechanism 168 is relatively large. In guide wire management systems employing a pivotable guide wire brake housing or clamp, the maximum pivot angle 208 may range from about 20° to about 160° and, more preferably, from about 60° to about 150°. In some embodiments, the maximum pivot angle 208 is at least about 45°.

In some embodiments, adjustable pivot mechanism 204 may incorporate one or more stops providing convenient positioning of the guide wire brake housing at any of a plurality of predetermined positions, providing a plurality of selectable pivot angles. In one embodiment, adjustment of pivot mechanism 204 may be user operable and may incorporate an adjustment mechanism (not shown), such as a thumb screw, knurled nut or other similar mechanism, that may be loosened and tightened by an operator to change pivot angle 208. The pivot angle 208 may be adjustable continuously and/or in pre-defined incremental steps.

When an operator repositions guide wire brake housing 160, changing pivot angle 208, the dimensions of the guide wire buffer zone also change, allowing the guide wire buffer zone to be selected, and adjusted, prior to or during an intervention according to the operator's anticipated or determined need for the distance of relative axial motion of the interventional catheter and/or operating head 108 with respect to the guide wire during the intervention. FIGS. 4A-6B illustrate, schematically, the progression that occurs during an intervention, both at the proximal end of the interventional catheter in the guide wire buffer zone and at the distal end of the interventional catheter as the catheter and/or operating head are advanced distally over the guide wire.

Figure 4A:
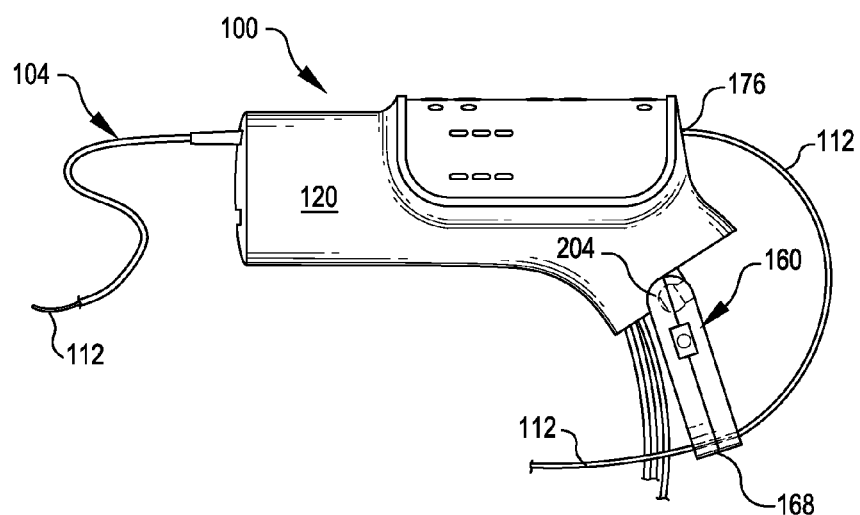
FIG. 4A is a schematic view of the interventional catheter assembly and guide wire management system of FIG. 3 illustrating an exemplary configuration when the interventional catheter is positioned on a guide wire proximal to and near a target intervention site, as illustrated schematically in FIG. 4B.
Figure 4B:
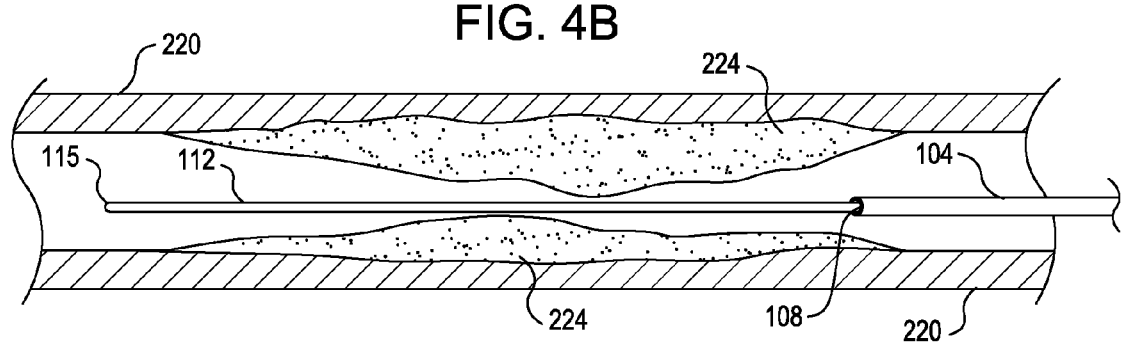

FIGS. 4A and 4B show the guide wire brake housing 160 positioned in a large guide wire buffer zone configuration and shows guide wire 112 as it would be in the guide wire buffer zone when the guide wire and interventional catheter are positioned as illustrated in FIG. 4B. FIG. 4B schematically illustrates a lesion or occlusion 224 in blood vessel 220, constricting blood flow through the vessel. An interventional catheter may be used, in this situation, to remove occlusive material from the vessel. In this type of intervention, a distal end 115 of guide wire 112 is navigated through the lesion and positioned generally distal to lesion 224. Interventional catheter 104 is navigated to the site, over guide wire 112, and positioned with a distal end of the interventional catheter, and operating head 104, generally proximal to occlusion 224. This is a neutral position of the interventional catheter with respect to the guide wire, and the guide wire is clamped in this position at guide wire clamp 168, forming a smooth, neutral condition curve in the guide wire buffer zone between guide wire entry/exit port 176 and guide wire clamp 168. The position of the guide wire brake housing 160 or guide wire brake 168 may be changed or adjusted to provide the dimension of the guide wire buffer zone desired, depending on the type and length of the lesion. A relatively large guide wire buffer zone is illustrated in FIG. 4A.

Figure 5A:
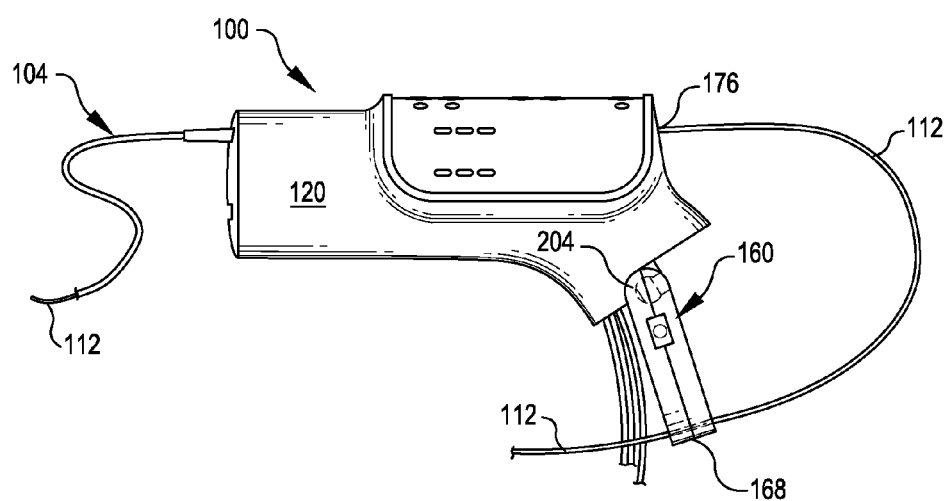
FIG. 5A is a schematic view of the interventional catheter assembly and guide wire management system of FIG. 3 illustrating an exemplary configuration when the interventional catheter has been advanced on the guide wire partially through an occlusion at a target intervention site, as illustrated schematically in FIG. 5B.
Figure 5B:
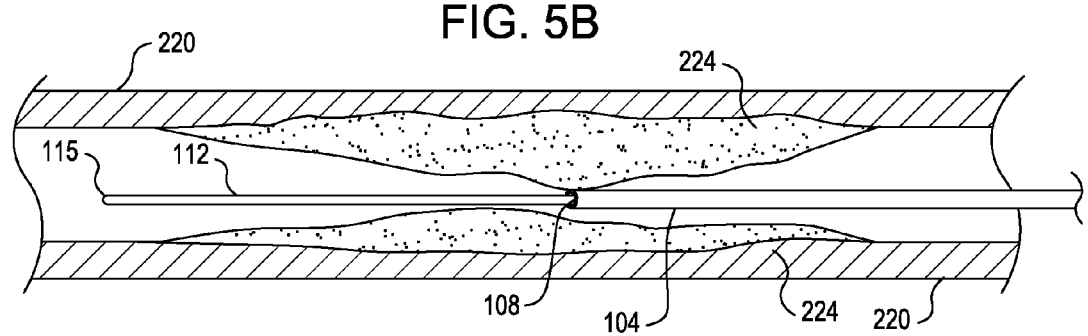

FIG. 5A shows the guide wire brake housing 160 and guide wire brake 168 positioned to provide a guide wire buffer zone as illustrated in FIG. 4A, and shows the length of guide wire 112 accumulated in the guide wire buffer zone when the guide wire and interventional catheter are positioned in the lesion as illustrated in FIG. 5B. FIG. 5B schematically illustrates lesion or occlusion 224 in blood vessel 220, with the interventional catheter 104 and operating head 108 advanced over the guide wire and positioned midway through the occlusion. Advancement of the interventional catheter relative to the guide wire produces an accumulation of guide wire length in the guide wire buffer zone just distal to the guide wire clamp, as illustrated in FIG. 5A, with the additional guide wire length accumulated in the guide wire buffer zone forming a generally larger profile curve than the curve formed by the guide wire in the neutral position shown in FIG. 4A.

Figure 6A:
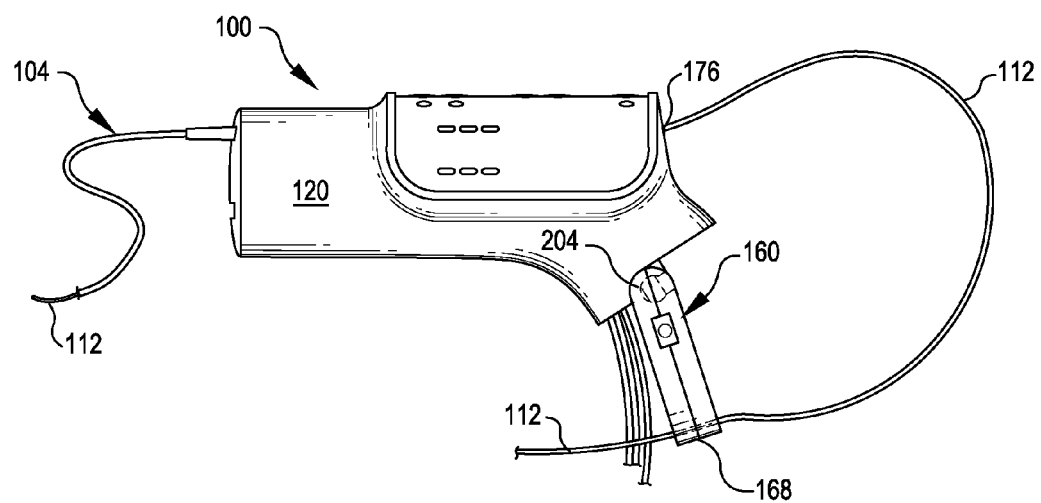
FIG. 6A is a schematic view of the interventional catheter assembly and guide wire management system of FIG. 3 illustrating an exemplary configuration when the interventional catheter has been advanced on the guide wire through the length of an occlusion at a target intervention site, as illustrated schematically in FIG. 6B.
Figure 6B:
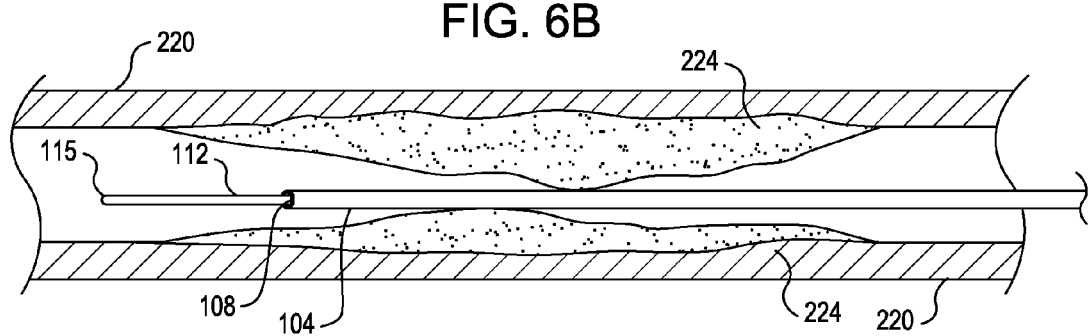

FIG. 6A shows the guide wire brake housing 160 positioned to provide the same guide wire buffer zone illustrated in FIGS. 4A and 5A, and shows a length of guide wire 112 accumulated in the guide wire buffer zone corresponding to the guide wire and interventional catheter positioned illustrated in FIG. 6B. FIG. 6B schematically illustrates a lesion or occlusion 224 in blood vessel 220 constricting blood flow through the vessel, with the interventional catheter 104 and operating head 108 advanced over the guide wire in a distal direction entirely through the occlusion. This further advancement of the interventional catheter relative to the guide wire produces additional accumulation of guide wire length in the guide wire buffer zone just distal to the guide wire clamp, producing larger curved segment of guide wire 112 in the guide wire buffer zone, as shown in FIG. 6A.

This progression illustrates the relative movement of the interventional catheter over the guide wire and the accumulation of excess guide wire length in the guide wire buffer zone during an exemplary interventional procedure. The guide wire buffer zone illustrated would permit the accumulation of additional guide wire length as well, allowing an intervention to proceed along a longer lesion without repositioning and reclamping the guide wire brake. Retracting the guide wire proximally through the lesion follows the same protocol in reverse, allowing guide wire length accumulated in the guide wire buffer zone to be relocated distally with respect to the catheter as the catheter is moved proximally. Retraction of the guide wire proximally through the lesion for withdrawal of the interventional catheter and operating head from the site, or for repositioning; of the operating head proximally of the lesion for another advance through the lesion, follows the pattern illustrated in FIGS. 4A-6B in reverse, with the length of excess guide wire diminishing and the curved profile formed by the length of guide wire accumulated in the guide wire buffer zone changing as the interventional catheter and operating head are moved proximally with respect to the distal end of the clamped guide wire.

FIG. 7 shows another embodiment of an interventional catheter of the present disclosure in which guide wire brake housing 160 is optionally detachable and removable from controller housing 120. In the embodiment shown in FIG. 7, release button 174 may be actuated by an operator to detach and remove guide wire brake housing 160 from pivot mount 170. The detached guide wire brake housing 160 may (optionally) remain connected to controller housing 120 by means of a tether 172, or another a flexible, retractable wire or cable. When detached from controller housing 120, guide wire brake housing 160 may be located and fixedly positioned independently of controller housing 120 using an integrated clamping mechanism or separately provided clamps. Detachment of the guide wire brake housing 160 and positioning it a distance from the guide wire exit port 176 and controller housing 120 allows the operator to select an additional range of guide wire buffer zone dimensions and configurations, allowing a greater range of interventional catheter and operating head displacement along the guide wire at the interventional site. Repositioning of the guide wire brake housing prior to or during an intervention also allows for the excess guide wire length to accumulate in a variety of non-linear curved profiles within the guide wire buffer zone. This feature may be especially useful during interventions that require a relatively large range of distal and/or proximal translation of the interventional catheter and/or operating head 108 over guide wire 112.

FIGS. 8A and 8B illustrate another interventional catheter assembly of the present disclosure having a guide wire management system employing a guide wire brake mounted to operate in a slot provided in an interventional catheter housing. Housing assembly 300 generally protects and may contain and/or enclose (partially or entirely) interventional catheter mechanisms and components such as drive motors, energy sources, electro-mechanical components, conduits, circuit boards, data processors, communication ports, fluid manifolds and the like, for operating the interventional catheter and/or an operating head. The configuration of the housing may be generally rectangular, as illustrated, or other configurations may be used. In some embodiments, the housing assembly is provided in combination with an interventional catheter and associated components and conduits as an integrally assembled unit that is ready for use as interventional catheter assembly. In other embodiments, the housing assembly may be provided as a separate component, with associated components, conduits and the like mounted to and/or with the housing prior to use. In some embodiments, the housing assembly may be intended as a single-use, disposable component; in other embodiments, the housing assembly may be provided as a re-usable component that may be cleaned and/or sterilized prior to each use.

Interventional catheter 304 is operably connected (or connectable) at a proximal region to housing 300 at catheter feedthrough 324. Flexible interventional catheter 304 comprises an elongated, flexible catheter configured to be at least partially inserted into and navigated through a lumen and/or cavity within a subject's body, and may embody any of a variety of types of interventional catheters, including simple aspiration and/or infusion catheters, delivery catheters for delivering implantable devices, interventional catheters having an operating head positioned or positionable in proximity to a distal end, or the like in embodiments in which an operating head is provided, the operating head may be operated to provide a desired diagnostic or treatment modality to an interventional site within a patient, as previously described. Housing assembly 300 may incorporate one or more user interface control features 332 (e.g., user operable switches and/or visual status indicators) providing a user interface for one or more monitoring or control features of the interventional catheter assembly.

In the embodiment illustrated in FIGS. 8A and 8B, aspiration conduit 348, infusion conduit 352 and electrical cable 358 enter housing assembly 300 at a location spaced apart from and generally opposite the location of catheter feedthrough 324, generally at the proximal region of housing 300 (when in use). Aspiration conduit 348 and infusion conduit 352 and electrical cable 358 operate as previously described, with aspiration and infusion conduits communicating with aspiration and infusion lumens of the elongated catheter.

FIGS. 8A and 8B schematically illustrate interventional catheter 304 mounted "over" a guide wire 312 for illustrative purposes as it would be for operation of the interventional catheter during an intervention. Guide wire 312 transits an interventional catheter guide wire lumen in, or a guidewire track or channel associated with, interventional catheter 304. During operation, the guide wire is positioned within the elongated catheter, with a distal end of guide wire 312 projecting from a distal end of interventional catheter 304. Guide wire 312 also traverses catheter feedthrough 324 and housing 300, exiting housing 300 at a generally proximal location at guide wire exit port 376. In many embodiments, a guide wire lumen or passageway transits housing 300 between catheter feedthrough 324 and guide wire exit port 376 along a substantially linear path to prevent bending and kinking of the guide wire.

Guide wire brake slot 360 is provided as a cavity or depression or slot in a surface of housing 300, spaced a distance from guide wire exit port 376. A guide wire brake mechanism (not visible), is positioned to operate within the slot, to releasably clamp a portion of guide wire 312 positioned within slot 360. The location and orientation of the guide wire exit port, in combination with the location and orientation of guide wire brake slot 360, changes the direction and path of guide wire 312 following its exit from port 376. In some embodiments, as shown, the path of the guide wire following its exit from port 376 curves and the guide wire then extends distally, toward the housing, and is received in guide wire brake slot 360 provided in housing 300.

The guide wire brake mechanism is preferably operable to clamp the guide wire, effectively preventing both translation and rotation of the guide wire when clamped. Thus, the guide wire brake mechanism is a user operable component that, in an open, released condition allows the guide wire to rotate and translate freely and in a closed, actuated condition serves to clamp the guide wire and prevent the guide wire from moving either axially or rotationally with respect to the guide wire brake mechanism and slot 360. This fixes the axial and rotational position of guide wire 312 with respect to the brake mechanism, the interventional catheter and operating head, and the intervention site, provided that the position of housing 300 and guide wire brake slot 360 remains unchanged.

In the exemplary embodiment illustrated in FIGS. 8A and 8B, housing 300 is generally rectangular (although many other configurations of the housing may be implemented), and guide wire exit port 376 and guide wire brake slot 360 are located at a common end region of housing 300, generally opposite the end region of the housing from which interventional catheter 304 extends distally during operation. In alternative embodiments, a guide wire exit port and guide wire brake slot may be provided at or along different housing surfaces or edges. The guide wire brake slot may be provided in a bottom wall or side wall of the housing, for example, rather than a top wall as shown in FIGS. 8A and 8B. The distance between the guide wire exit port and guide wire brake slot is sufficient to prevent a guide wire exiting the guide wire exit port and positioned in the guide wire brake slot from kinking or bending. Suitable distances will depend on the size and properties of the guide wire and the orientation of the exit port and guide wire brake slot. The length of the guide wire slot may vary depending on the type and application of the interventional catheter, and the properties of the guide wire.

In the embodiment illustrated in FIGS. 8A and 8B, guide wire brake slot 360 is provided at an angled orientation with respect to the angle at which guide wire 312 exits housing 300 at guide wire exit port 376. The angle formed at the intersection of an extension of the guide wire as it exits housing 300 at guide wire exit port 376 and an extension of guide wire slot 360, proximally of housing, in some embodiments is from about 15° to about 120°; in other embodiments, the angle formed may be from about 15° to about 100°; in yet other embodiments, the angle formed may be from about 20° to about 80°; and in still other embodiments, the angle formed may be greater than about 15° and/or less than about 60°. In the embodiments illustrated in FIGS. 8A and 8B, the path of guide wire 312 is generally orthogonal to the proximal end of housing 300 as it exits guide wire exit port 376. An extension of slot 360 as shown in FIGS. 8A and 8B forms an angle of approximately 30° with the path of guide wire 312 as it exits guide wire exit port 376. In some embodiments, the guide wire brake slot has an angular orientation, as described above, with respect to at least one peripheral side of the housing assembly.

In the embodiment illustrated in FIGS. 8A and 8B, the space between guide wire entry/exit port 376 and the entry to guide wire brake slot 360 defines a guide wire buffer zone, as previously described, which guide wire 312 transits along a curved path in a substantially unrestrained and generally unsupported condition. In the configuration shown in FIG. 8A, a relatively short length of guide wire 312 is present in the guide wire buffer zone between guide wire exit port 376 and the entry to guide wire brake slot 360. This represents a "neutral" condition of the guide wire in the guide wire buffer zone that corresponds to the relative positions of the guide wire and interventional catheter prior to advancing the interventional catheter distally over the guide wire at the intervention site, as schematically shown in FIG. 4B.

In the configuration shown in FIG. 8B, a longer length of guide wire 312 is present in the guide wire buffer zone between guide wire exit port 376 and the entry to guide wire brake slot 360. This represents a condition of the guide wire that corresponds to the relative positions of the distal end of the guide wire and interventional catheter when the interventional catheter 304 has been advanced distally over the guide wire and through the occlusion, as shown in FIG. 6B. This advancement of the interventional catheter distally over the guide wire produces additional accumulation of guide wire length in the guide wire buffer zone, producing a larger curved segment of guide wire 312 in the guide wire buffer zone between guide wire exit port 376 and the entry to guide wire brake slot 360.

This progression illustrates the relative movement of the interventional catheter over the guide wire and the accumulation of excess guide wire length in the guide wire buffer zone during an exemplary interventional procedure. The arrangement of the guide wire exit port 376 and the guide wire brake slot 360 permits the accumulation of additional guide wire length, allowing an intervention to proceed along a longer zone of intervention without repositioning and reclamping the guide wire brake. Retracting the catheter proximally through the zone of intervention follows the same protocol in reverse, allowing guide wire length accumulated in the guide wire buffer zone to be relocated distally with respect to the catheter as the catheter is moved proximally.

Many interventional procedures involve advancing and retracting a catheter over a guide wire along a zone of intervention, in some embodiments, aspirating and/or infusing catheters are advanced and then retracted through an interventional zone while aspirating and/or infusing. In some embodiments, delivery catheters are positioned at different locations in an interventional zone during placement or retrieval of an implantable device. In other embodiments, interventional catheters having a operating head may make several passes through an occlusion, removing additional occlusive material with each pass, or to accomplish other interventional objectives. Providing a guide wire buffer zone in accordance with the present disclosure, and arranging a guidewire entry/exit port and guide wire brake position to provide a functional guide wire buffer zone, allows an operator to advance the catheter distally over the wire for a long distance, and to make multiple sequential catheter advances and retractions without repositioning and re-clamping the guide wire.

While the present disclosure has been described with reference to the accompanying drawings in which particular embodiments are shown and explained, it is to be understood that persons skilled in the art may modify the embodiments described herein without departing from the spirit and broad scope of the claimed invention. Accordingly, the descriptions provided herein are considered to be illustrative and exemplary of specific structures, aspects and features within the broad scope of the present disclosure and not as limiting the scope of the claimed invention.

We claim:

1. An interventional catheter housing assembly comprising: a housing having a top wall, a bottom wall, and a plurality of side walls enclosing at least one interventional catheter operating component; a catheter feedthrough penetrating the housing; a guide wire exit port for slidably receiving a guide wire; an angled slot provided in the top wall, the bottom wall, or a side wall of the housing and positioned a distance from the guide wire exit port; wherein the guide wire exit port and the angled slot penetrate a common side wall of the housing, and a guide wire clamp provided within the housing and positioned for operating within the angled slot that, in a closed, actuated condition prevents both rotation and axial translation of the guide wire positioned in the angled slot.

2. The interventional catheter housing assembly of claim 1, wherein the catheter feedthrough is positioned at a first housing location and the guide wire exit port is positioned at a housing location spaced from and generally opposite the first housing location.

3. The interventional catheter housing assembly of claim 1, wherein the angled slot is arranged at an angle of greater than 15° and less than 60° with respect to the path of the guide wire as it exits the guide wire exit port.

4. The interventional catheter housing assembly of claim 1, wherein the angled slot is arranged at an angle of from about 20° to about 80° with respect to the path of the guide wire as it exits the guide wire exit port.

5. The interventional catheter housing assembly of claim 1, wherein the housing is generally rectangular and the angled slot has an angular orientation forms an angle of from 20° to 80° with respect to at least one peripheral side wall of the generally rectangular housing.

6. The interventional catheter housing assembly of claim 1, wherein the angled slot is provided in the top wall or the bottom wall of the housing, the side walls are perimeter side walls, and a first end of the angled slot interrupts a first perimeter side wall of the housing, while a second end of the angled slot interrupts a second perimeter side wall.

7. The interventional catheter housing assembly of claim 1, wherein the housing incorporates user interface control features for controlling operation of an interventional catheter.

8. An interventional catheter assembly comprising: an elongated flexible catheter sized and configured to be navigated to an internal interventional site and having a guide wire lumen; a controller housing communicating with the elongated flexible catheter and having a top wall, a bottom wall, and a plurality of side walls enclosing at least one interventional catheter operating component; a catheter feedthrough penetrating the housing where the elongated flexible catheter is operably connected to the housing; a guide wire exit port penetrating the housing for slidably receiving a guide wire; an angled slot penetrating at least one of the top wall, the bottom wall, and a side wall of the housing at an angle to the path of the guide wire as it exits the guide wire exit port and positioned a distance from the guide wire exit port; wherein the guide wire exit port and the angled slot penetrate a common side wall of the housing, and a guide wire clamp provided within the housing and positioned for operating within the angled slot that, in a closed, actuated condition prevents both rotation and axial translation of the guide wire positioned in the angled slot.

9. The interventional catheter assembly of claim 8, additionally comprising an operating head positioned or positionable in proximity to a distal end of the elongated flexible catheter.

10. The interventional catheter assembly of claim 9, wherein the operating head is operably connected to a rotatable and axially translatable drive shaft.

11. The interventional catheter assembly of claim 8, additionally comprising an aspiration conduit communicating with the housing.

12. The interventional catheter assembly of claim 8, additionally comprising an infusion conduit communicating with the housing.

13. The interventional catheter assembly of claim 9, wherein the operating head comprises a material removal device selected from the group consisting of: one or more cutter or ablation elements; an abrasive surface of a rotational element; a plaque excision device; a laser ablation device; a high frequency ultrasound ablation device; a radio frequency device; a heat-producing device; and an electrical device that operates to remove unwanted material from body lumens or cavities without rotating.

14. The interventional catheter assembly of claim 8, additionally comprising an electrical cable operably connected to the housing.

15. The interventional catheter assembly of claim 8, wherein the angled slot penetrates at least one of the top wall and the bottom wall, and additionally penetrates two side walls of the housing.

16. The interventional catheter assembly of claim 8, wherein the housing is generally rectangular and the angled slot forms an angle of from 20° to 80° with respect to at least one peripheral side wall of the generally rectangular housing.

17. The interventional catheter assembly of claim 8, wherein the angled slot is provided in a sidewall of the housing.

18. The interventional catheter housing assembly of claim 1, wherein the angled slot is provided in a sidewall of the housing.

* * * * *